United States Patent [19]  
Braid et al.

[11] 4,273,665  
[45] Jun. 16, 1981

[54] FRICTION REDUCING ADDITIVES AND COMPOSITIONS THEREOF

[75] Inventors: Milton Braid, Westmont; Andrew G. Horodysky, Cherry Hill; Joan M. Kaminski, Clementon, all of N.J.

[73] Assignee: Mobil Oil Corporation, New York, N.Y.

[21] Appl. No.: 83,068

[22] Filed: Oct. 9, 1979

[51] Int. Cl.$^3$ ............................................. C10M 1/32
[52] U.S. Cl. ................................ 252/49.6; 252/51.5 R
[58] Field of Search ...................... 252/51.5 R, 49.6

[56] References Cited

U.S. PATENT DOCUMENTS

| | | | |
|---|---|---|---|
| 2,991,249 | 4/1961 | Andress et al. | 252/40 |
| 3,195,332 | 7/1965 | Ranauto | 252/51.5 R |
| 3,634,256 | 1/1972 | Bickham | 252/51.5 R |

*Primary Examiner*—Jacqueline V. Howard  
*Attorney, Agent, or Firm*—C. A. Huggett; M. G. Gilman; H. M. Flournoy

[57] ABSTRACT

Hydrolysis products of 1-(2-hydroxyalkyl)-2-alkyl- or alkenyl imidazolines and borated adducts of hydrolyzed 1-(2-hydroxyethyl)-2-alkylimidazolines are highly effective friction reducing or friction modifying additives when incorporated into lubricating compositions.

20 Claims, No Drawings

FRICTION REDUCING ADDITIVES AND COMPOSITIONS THEREOF

BACKGROUND OF THE INVENTION

1. Field of the Invention

This invention relates to lubricant additives and compositions thereof and, more particularly, to lubricant compositions comprising oils of lubricating viscosity or greases prepared therefrom containing a minor friction reducing amount of hydrolysis products of substituted imidazolines and borated adducts of such hydrolysis products.

2. Description of the Prior Art

Many means have been employed to reduce overall friction in modern engines, particularly automobile engines. The primary reasons are to reduce engine wear thereby prolonging engine life and to reduce the amount of fuel consumed by the engine thereby reducing the engine's energy requirements or fuel consumption. While it is commonly understood that lubricants by definition, reduce friction between moving surfaces, friction reducing additives are agents which when added to lubricants in minor amounts significantly enhance the frictional properties of those lubricants without modifying other physical properties such as viscosity, density, pour point, and the like.

Many of the solutions to reducing fuel consumption have been strictly mechanical, as for example, setting the engines for a leaner burn or building smaller cars and smaller engines. However, considerable work has been done with lubricating oils, mineral and synthetic, to enhance their friction properties by modifying them with friction reducing additives.

Although imidazolines have been added to lubricants, for various purposes, the hydrolysis products of this invention and the corresponding borated derivatives are to applicants' best knowledge novel and have no prior history of use as friction reducing or friction modifying additives or for that matter of use in the major additive areas of anti-corrosion or antioxidation in lubricating compositions. It is further understood that the borated derivatives of this invention possess multifunctional capabilities, i.e., antioxidation and/or bearing corrosion protection in addition to friction modification.

SUMMARY OF THE INVENTION

The additive compounds useful in this invention are fully or partially hydrolyzed products of 2-hydroxyalkyl-alkyl (or alkenyl) imidazolines, represented by structure I

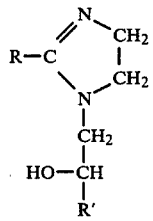

wherein R is an alkyl or alkenyl group containing from 9 to about 29 carbon atoms and R' is hydrogen or an alkyl group containing from 1 to about 6 carbon atoms, and boron-containing derivatives thereof.

The invention is also directed to lubricant compositions having reduced friction containing such hydrolysis products and to a method of reducing fuel consumption in internal combustion engines by treating the moving surfaces thereof with said composition.

The amount of additive in the lubricant compositions may range from 0.1 to about 10% by weight of the total lubricant composition. Preferred in from about 0.5 to 5 wt. %.

The compositions hereof can also include other materials, such as, corrosion inhibitors, viscosity index improvers, extreme pressure agents, all of which impart their customary properties to the particular compositions and do not detract from the value of the compositions into which they are incorporated. Generally the total amount of all such other materials will not exceed about 10 to 20 wt. %.

The lubricants contemplated for use herein include both mineral and synthetic hydrocarbon oils of lubricating viscosity, mixtures of mineral and synthetic oils, and greases prepared therefrom and other solid lubricants. The synthetic oils may include polyisobutylenes, hydrogenated olefins, polypropylene glycol, di(2-ethylhexyl) sebacate, dibutyl phthalate, neopentyl esters, pentaerythritol esters, trimethylol propane esters, fluorocarbons, silicate esters, silanes, hydrogenated mineral oils, chain-type polyphenyls, siloxanes and silicones, phenoxy phenylethers.

The additive compounds in accordance with the invention may be prepared by reaction of the aforementioned imidazoline with water optionally in the presence of a catalyst. Repesentative hydrolysis products are depicted by structures II and III below but are not limited thereto:

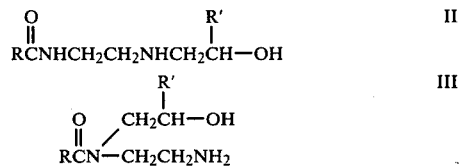

A stoichiometric amount of water can be used or as much as a 4 mole excess. The reaction solvent can be any suitable low boiling alcohol, such as ethanol or butanol. Although an acid catalyst such as hydrochloric acid or acetic acid can be used for the hydrolysis reaction, the imidazoline will nevertheless hydrolyze in the absence of any catalyst. The reaction time can vary from 1 to 6 hours. Preferred reaction time is 3 hours.

The borated products or derivatives include structures depicted below as IV, V, VI and VII.

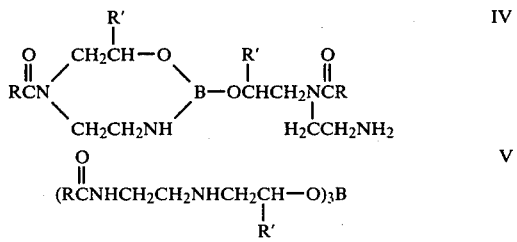

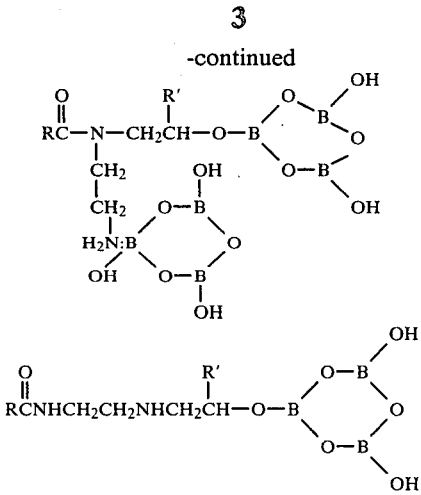

wherein R and R' are as defined hereinabove.

Any suitable boration means known to the art may be used as for example boric acid or a transesterification reaction with a trialkyl borate.

Butanol, toluene, xylene or the like can be used as solvent. Stoichiometric amounts of boric acid can be used or as much as 2 mole excess can be used. Usually, 65 to 70% of the molar amount of water is obtained relative to the amount of boric acid used. Boration reaction temperatures can vary from 110° to 180° C. with a preferred range of from about 120° to 160° C.

Having described the invention in general terms, the following are offered as specific illustrations thereof. It is to be understood they are illustrations only and that the invention is not thereby limited except as by the appended claims.

DESCRIPTION OF SPECIFIC EMBODIMENTS

EXAMPLE 1

The base oil used in the low velocity friction apparatus was a fully formulated SAE 5W-20 synthetic engine oil.

EXAMPLE 2

Partial (ring opening) hydrolysis of 1-(2-hydroxyethyl)-2-heptadecenylimidazoline A mixture of 1-(2-hydroxyethyl)-2-heptadecenylimidazoline (59.5 g), water (9.5 g) and denatured ethanol (43.3 g) was heated in a boiling water bath while stirring for about 2 hours. At the end of this reaction period alcohol solvent and unreacted water were removed by rotary film evaporation under reduced pressure at a maximum pot temperature of 100° C. Remaining was the ring-opened reaction product showing a carbonyl absorption band at about 1650 cm$^{-1}$ in addition to the carbon-nitrogen non-ring-opened imido absorption band at about 1600 cm$^{-1}$. This product was a tan colored semi-solid.

EXAMPLE 3

Acid-catalyzed (ring-opening) hydrolysis of 1-(2-hydroxyethyl)-2-heptadecenylimidazoline A mixture of 1-(2-hydroxyethyl)-2-heptadecenylimidazoline (70.5 g), water (16.8 g), ethanol (16.2 g) and concentrated hydrochloric acid (2.0 g) was stirred and heated in a boiling water bath for about 1 hr. After work-up there was obtained as a tan waxy solid the ring-opened reaction product. The infrared spectrum of the product differed significantly from that of the reactant imidazoline, principally in the disappearance of the carbon-nitrogen imido band at about 1600 cm$^{-1}$ and the appearance of a strong carbonyl absorption band in the 1640–1650 cm$^{-1}$ region indicating complete ring opening.

EXAMPLE 4

Boration of hydrolyzed 1-(2-hydroxyethyl)-2-heptadecenylimidazoline

A mixture of hydrolyzed 1-(2-hydroxyethyl)-2-heptadecenyl imidazoline (100 g), prepared as described in Example 3, boric acid (11.2 g), and butanol (96 g) was refluxed at 115° to 155° C. until all the water formed in the reaction azeotroped off (6.5 cc, 4 hrs.). The alcohol solvent was removed by high speed rotary evaporation under reduced pressure at 100° C. The resulting product was filtered through diatomaceous earth and was a viscous, brown transparent oil. The infrared spectrum of the product still contained a strong carbonyl absorption in the 1640–1650 cm$^{-1}$ region indicating that the hydrolyzed 1-(2-hydroxyethyl)-2-heptadecenylimidazoline starting material had not recyclized.

EXAMPLE 5

Ring-opening hydrolysis of 1-(2-hydroxyethyl)-2-heptadecylimidazoline

A mixture of 1-(2-hydroxyethyl)-2-heptadecylimidazoline (40 g), water (9.4 g), and ethanol (9.6 g) was stirred and heated at 90° C. for 3 hours. The water and ethanol were removed by high speed rotary evaporation, and the resulting product was a golden waxy solid. The infrared spectrum of the product contained a strong carbonyl absorption band in the 1640–1650 cm$^{-1}$ region and showed no characteristic imidazoline carbon-nitrogen imido band at 1600 cm$^{-1}$, thereby, indicating complete ring-opening of the starting imidazoline.

EXAMPLE 6

Boration of hydrolyzed 1-(2-hydroxyethyl)-2-heptadecylimidazoline

A mixture of hydrolyzed 1-(2-hydroxyethyl)-2-heptadecylimidazoline (26 g) prepared as described in Example 5, boric acid (8.8 g), and toluene (117 g) was refluxed at 120° to 150° C. until all the water that formed in the reaction azeotroped off (5.4 cc). The reaction mixture was diluted with 26 g of a low viscosity, low volatility process oil to reduce the viscosity of the final product. The toluene solvent was stripped off and the resulting product was a dark brown viscous solid. The infrared spectrum of the product conformed to the expected structure.

The additives prepared as above were then incorporated into a fully formulated engine oil (Example 1) and evaluated using the Low Velocity Friction Apparatus.

EVALUATION OF THE PRODUCT

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

PROCEDURE

The rubbing surfaces and 12–13 ml. of test lubricant are placed on the LVFA. A 500 psi load is applied, and the sliding speed is maintained at 30 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of oil plus additive})}{(U_k \text{ of oil alone})} \times 100$$

Thus, the value for the oil alone would be zero for the form of the data used in the Table below.

TABLE

| Example No. | Additive Conc. | % Change in Coefficient of Friction at | |
|---|---|---|---|
| | | 5 Ft./Min. | 30 Ft./Min. |
| 1 | — | 0 | 0 |
| 2 | 4% | 26 | 19 |
| 3 | 4% | 35 | 32 |
| 4 | 4% | 46 | 34 |
| 4 | 2% | 44 | 28 |
| 5 | 2% | 16 | — |

From the data in the above Table it is readily apparent that the subject hydrolysis products significantly improve the friction reducing properties of lubricants into which they are incorporated. Moreover, the borated hydrolyzed heptadecenylimidazoline of Example 4 at 2% (wt. conc.) reduces friction almost as well (at 30 ft./min.) and better than (at 5 ft./min.) the non-borated additive of Example 2 at 4%.

It is understood by those of ordinary skill in the art that variations of this invention within the scope thereof can be readily made.

We claim:

1. A lubricant composition comprising a major proportion of an oil of lubricating viscosity or a grease prepared therefrom and a minor effective proportion of a friction reducing or friction modifying additive selected from the group consisting of a hydrolyzed derivative of a 1-(2-hydroxyalkyl)-2-alkylimidazoline, a 1-(2-hydroxyalkyl)-2-alkenylimidazoline and borated derivatives thereof wherein said alkyl or alkenyl portion of said imidazoline contains from about 9 to 29 carbon atoms and said alkyl portion of the hydroxyalkyl moiety contains from 1 to 6 carbon atoms.

2. The composition of claim 1 wherein said additive is partially hydrolyzed 1-(2-hydroxyethyl)-2-heptadecenylimidazoline.

3. The composition of claim 1 wherein said additive is fully hydrolyzed 1-(2-hydroxyethyl)-2-heptadecenylimidazoline.

4. The composition of claims 2 or 3 wherein said additives is borated.

5. The composition of claim 1 wherein said additive is fully or partially hydrolyzed 1-(2-hydroxyethyl)-2-heptadecylimidazoline.

6. The compound of claim 5 wherein said additive is borated.

7. The composition of claim 1 wherein said composition comprises an oil of lubricating viscosity.

8. The composition of claim 7 wherein said oil is a mineral or refined petroleum oil.

9. The composition of claim 7 wherein said oil of lubricating viscosity is a synthetic oil.

10. The composition of claim 7 wherein said oil of lubricating viscosity is a mixture of mineral and synthetic oils.

11. The composition of claim 9 wherein the oil of lubricating viscosity is a mixture of synthetic oils.

12. The composition of claim 1 wherein said composition comprises a grease.

13. The composition of claim 1 containing from 0.1 to about 10 wt. % of said additive.

14. The composition of claim 13 containing about 0.25 to 4 wt. % of said additive.

15. A method of reducing fuel consumption in an internal combustion engine by treating the moving surfaces thereof with a lubricant composition comprising a major proportion of an oil of lubricating viscosity and a minor effective amount of a friction reducing or friction modifying additive consisting of a fully or partially hydrolyzed derivative of a
   1-(2-hydroxyalkyl)-2-alkylimidazoline, a
   1-(2-hydroxyalkyl)-2-alkenylimidazoline or borated derivatives thereof wherein said alkyl or alkenyl portion of said imidazoline has from about 9 to about 29 carbon atoms and said alkyl portion of the hydroxyalkyl moiety has from 1 to about 6 carbon atoms.

16. The method of claim 15 wherein said additive is partially hydrolyzed 1-(2-hydroxyethyl)-2-heptadecenylimidazoline.

17. The method of claim 15 wherein said additive is fully hydrolyzed 1-(2-hydroxyethyl)-2-heptadecenylimidazoline.

18. The method of claims 15 or 16 wherein said imidazolines are borated.

19. The method of claim 15 wherein said additive is fully or partially hydrolyzed 1-(2-hydroxyethyl)-2-heptadecylimidazoline.

20. The method of claim 15 wherein the oil of lubricating viscosity is a mineral or synthetic oil or mixtures thereof.

* * * * *